United States Patent [19]

Kaplan

[11] 4,345,103

[45] Aug. 17, 1982

[54] HYDROXYMETHYLATION OF THE CARBON RESIDUE OF ORGANOSILICON COMPOUNDS

[75] Inventor: Leonard Kaplan, Dunbar, W. Va.

[73] Assignee: Union Carbide Corporation, Danbury, Conn.

[21] Appl. No.: 278,898

[22] Filed: Jun. 29, 1981

[51] Int. Cl.³ .............................................. C07C 29/00
[52] U.S. Cl. .................................. 568/840; 568/715; 568/842; 518/700
[58] Field of Search ....................... 568/840, 842, 715

[56] References Cited

U.S. PATENT DOCUMENTS

| | | | |
|---|---|---|---|
| 2,485,366 | 10/1949 | Di Giorgio et al. | 568/840 |
| 2,626,272 | 1/1953 | Speier | 568/852 |
| 3,449,384 | 6/1969 | Ender | 568/840 |
| 4,076,758 | 2/1978 | Owsley et al. | 568/852 |
| 4,144,401 | 3/1979 | Wall | 568/840 |

*Primary Examiner*—Joseph E. Evans
*Attorney, Agent, or Firm*—Gary L. Wamer

[57] ABSTRACT

This invention relates to the manufacture of alcohols and derivatives thereof from the carbon residue of an organosilicon compound such that the resulting alcohol and derivatives thereof contain one carbon and one oxygen more than said carbon residue.

7 Claims, No Drawings

HYDROXYMETHYLATION OF THE CARBON RESIDUE OF ORGANOSILICON COMPOUNDS

BACKGROUND OF THE INVENTION

This invention relates to a process, and the catalyst which achieves this process, for making alcohols from synthesis gas, i.e., mixtures of hydrogen and carbon monoxide. More particularly the invention relates to the reaction of an organosilicon compound in the presence of a catalyst which is a ruthenium carbonyl complex wherein said organosilicon compound has at least one substituent such that the substituent-silicon bond will add across a transition metal, e.g. hydrogen bonded to silicon, and a carbon residue R—.

Earlier relevant studies fall into the categories of: (1) "insertion" of a transition metal into a Si—C bond (cleavage of a Si—C bond by a transition metal) and (2) "insertion" of a carbonyl unit into a Si—C bond.

The general potential of a transition metal compound to cleave the silicon-carbon bond in an organosilicon compound has been discussed by I. S. Akhrem, D. V. Avetisyan, R. S. Vartanyan, K. G. Shakhatuni, and M. E. Vol'pin, Izv. Akad. Nauk SSSR, 2327 (1975).

The reaction of iron carbonyls with silicon hetercycles, for example:

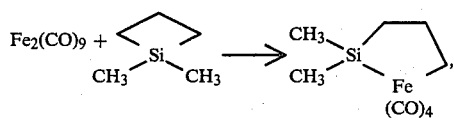

has been reported by C. S. Cundy, M. F. Lappert, J. Dubac, and P. Mazerolles, J. C. S. Dalton, 910 (1976); C. S. Cundy and M. F. Lappert, Chem. Comm., 445 (1972); and C. S. Cundy and M. F. Lappert, J. C. S. Dalton, 665 (1978). No reaction with Fe₂(CO)₉ was observed when the silicon heterocycle was

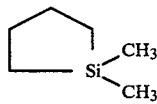

Further, no transition metal-silicon complex was isolated from the attempted reaction of the silacyclobutane and metal complexes of Cr, Mo, Mn, Ru, Co, Pt, Ir and Zr wherein, in most cases, no appreciable reaction was reported to have occurred.

Also,

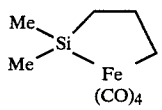

did not react with H₂ or CO in benzene up to reflux temperature.

The reaction:

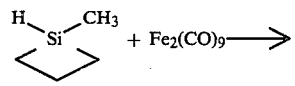

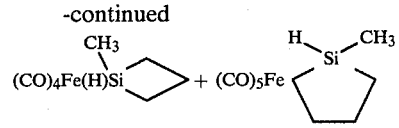

was reported by C. S. Cundy and M. F. Lappert, J. Organometal. Chem., 144, 317 (1978). Further, C. S. Cundy, C. Eaborn, and M. F. Lappert, J. Organometal. Chem., 44, 291 (1972) reported a study on polymerization of organosilanes and proposed the reaction:

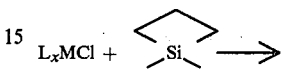

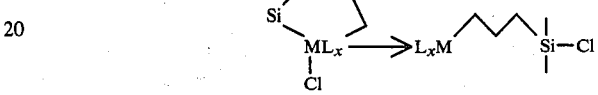

wherein R=X and is CH₃, —OCH₃ or R=CH₃ when X is Cl.

The reaction:

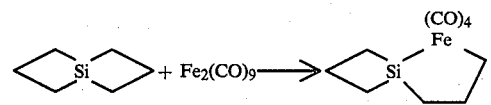

was reported by O. V. Kuz'min, A. L. Bykovets, V. M. Vdovin, and A. M. Krapavin, Izv. Akad. Nauk SSSR, 2815 (1979).

The cleavage of the silicon/carbon bond in organosilicon compounds by compounds of the platinum group metals Pt, Rh, Pd, Ru, Os and Ir were studied and reported by I. S. Akhrem, R. S. Vartanyan, N. M. Chistovalova, E. I. Mysov and M. E. Vol'pin, Izv. Akad. Nauk SSSR, 2069 (1976); I. S. Akhrem, N. M. Chistovalova, E. I. Mysov, and M. E. Vol'pin, Zh. Obshch. Khim., 42, 1868 (1972). The reaction of (CH₃)₄Si, (CH₃)₃Si(C₂H₅), (CH₃)₃SiC₄H₉ and (CH₃)₃Si(C₆H₅) were studied and cleavage of the silicon-carbon bond observed.

The palladium-catalyzed addition of an organosilicon compound:

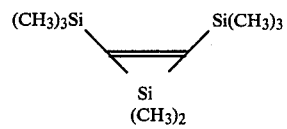

to alkynes and a diene to give an addition product has been reported by D. Seyferth, S. C. Vick, M. C. Shannon, T. F. O. Lim, and D. P. Duncan, J. Organometal, Chem., 135, C37 (1977). Exemplary of the addition reaction reported therein is:

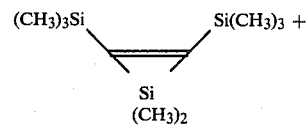

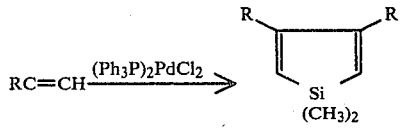

wherein R is (CH$_3$)$_3$C or CH$_3$C=CH$_2$. Similarly, where R is C$_6$H$_5$ was reported by D. Seyferth, D. P. Duncan, and S. C. Vick, J. Organometal. Chem, 125, C5 (1977).

For additional reports of the cleavage of a Si—C bond by a transition metal, see H. Sakurai, Y. Kamiyama, and Y. Nakadaira, J. Am. Chem. Soc., 99, 3879 (1977); M. Ishikawa, T. Fuchikami, and M. Kumada, Chem. Comm., 352 (1977); D. Mansuy, J. F. Bartoli, and J. C. Chottard, J. Organometal. Chem., 77, C49(1974); D. Mansuy, J. Pusset, and J. C. Chottard, J. Organometal. Chem., 105, 169 (1976); D. Mansuy, J. F. Bartoli, and J. C. Chottard, J. Organometal. Chem., 71, C32 (1974); I. S. Akhrem, N. M. Chistovalova, E. I. Mysov, and M. E. Vol'pin, J. Organometal. Chem., 72, 163 (1974); J. M. Kliegman, J. Organometal. Chem., 29, 73 (1971); C. G. Pitt and K. R. Skillern, J. Organometal, Chem., 7, 525 (1967); K. R. Beck and R. A. Benkeser, J. Organometal. Chem., 21, P35 (1970); D. R. Wegenberg and L. E. Nelson, J. Org. Chem., 30, 2618 (1965); M. R. Stober, M. C. Musolf, and J. L. Speier, J. Org. Chem., 30, 1651 (1965); E. M. Haschke and J. W. Fitch, J. Organometal. Chem., 57, C93 (1973); H. Gilman and D. H. Miles, J. Org. Chem., 23, 326 (1958); J. E. Poist and C. S. Krainhanzel, Chem. Comm., 607 (1968); N. S. Nametkin, V. M. Vdovin, and P. L. Grinberg, Izv. Akad. Nauk SSSR, 1133 (1964); W. P. Weber, R. A. Felix, A. K. Willard, and K. E. Koenig, Tet. Lett., 4701 (1971); I. S. Akhrem, N. M. Chistovalova, S. M. Airapetyan, E. I. Mysov, and M. E. Vol'pin, Izv. Akad. Nauk SSSR, 1126 (1978); J.-i. Yoshida, K. Tamao, M. Takahashi, and M. Kumada, Tet. Lett., 2161 (1978); I. S. Akhrem, D. V. Avetisyan, R. S. Vartanyan, K. G. Shakhatuni, and M. E. Vol'pin, Izv. Akad. Nauk SSSR, 2327 (1975).

In the category of "insertion" of a carbonyl unit into a Si—C bond, D. Seyferth, D. P. Duncan, and S. C. Vick, J. Organometal. Chem., 125, C5 (1977) reported the reaction:

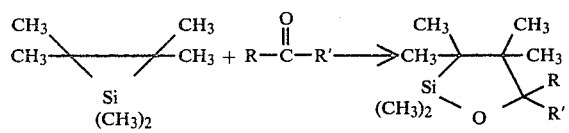

wherein R is phenyl and R' is methyl. Similarly, D. Seyferth, S. C. Vick, M. L. Shannon, T. F. O. Lim and D. P. Duncan, J. Organometal Chem., 135, C37 (1977) reported the reactions:

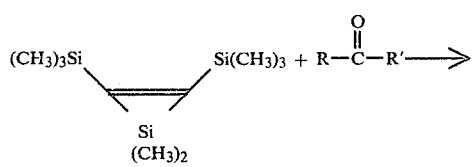

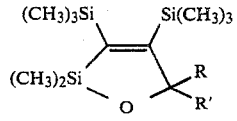

wherein R is H or CH$_3$; R' is CH$_3$.

E. W. Abel and R. J. Rowley, J. Organometal. Chem., 84, 199 (1975) reported the reaction:

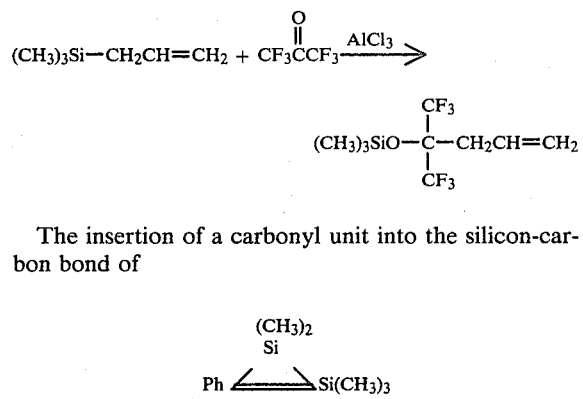

The insertion of a carbonyl unit into the silicon-carbon bond of

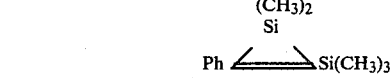

has been reported by H. Sakurai, Y. Kamiyama and Y. Nakadaira, J. Am. Chem. Soc., 99, 3879 (1977).

R. Calas, J. Dunogues, G. Deleris, and F. Pisciotti, J. Organometal. Chem., 69, C15 (1974); and G. Deleris, J. Dunogues and R. Calas, J. Organometal. Chem., 93, 43 (1975) generally report the reaction of carbonyl containing compounds and organosilicon compounds. For example:

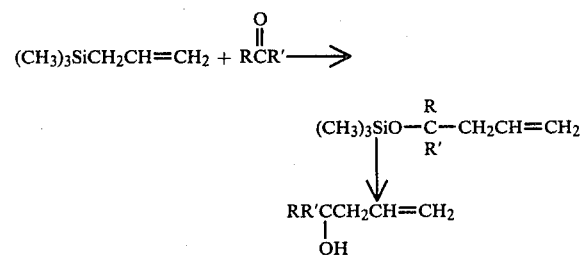

wherein R=CCl$_3$, R'=H; R=CH$_3$, R'=CH$_2$Cl.

For additional examples of the "insertion" of a carbonyl group into a Si—C bond see B. A. Gostevskii, O. A. Kruglaya, A. I. Albanov, and N. S. Vyazankin, J. Organometal. Chem., 187, 157 (1980) and the references cited therein.

The above discussion provides a brief characterization of the technology heretofore published or filed upon which relates to the hydroxymethylation of a carbon residue bonded to a silicon atom. The instant process is to be distinguished from the aforementioned processes in that there has been no previous report of the hydroxymethylation of a carbon residue bonded to a silicon atom nor has there been a report of the insertion of CO into such a silicon-carbon bond. The source of the carbonyl group in the instant process is carbon monoxide and is generally derived from synthesis gas. Synthesis gas is a source of such carbonyl groups that can be produced from non-petroleum sources.

SUMMARY OF THE INVENTION

In accordance with the present invention there is provided a process for preparing alcohols and derivatives thereof having one carbon and one oxygen more than that contained in the carbon residue (a carbon-containing substituent with carbon bonded to silicon) of an organosilicon compound and having a group (X) bonded to silicon wherein X is a group such that a transition metal can add across its bond to silicon, e.g. H, NR$_2$, halogen and the like. The process is carried out by reacting a mixture comprising oxides of carbon and hydrogen in the presence of a catalytically effective amount of a ruthenium carbonyl complex and said organosilicon compound.

DESCRIPTION OF THE INVENTION

This process constitutes a relatively low pressure process for converting synthesis gas to alcohols and derivatives thereof having one carbon and one oxygen more than that contained in the carbon residue of an organosilicon compound. The process of this invention is carried out in the liquid phase in the presence of a ruthenium carbonyl complex and an organosilicon compound, generally in a solution of the organosilicon compound, even though the ruthenium carbonyl complex may exist during the reaction in more than one liquid phase. In this sense, the reaction is termed a homogeneous liquid phase reaction. There may be more than one such phase existing in the reaction zone but the catalyst is always dissolved in at least one of such phases and is always in a dissolved liquid state.

The process of this invention involves the reaction of synthesis gas in the presence of soluble ruthenium complexes and an organosilicon compound at temperatures and pressures for a period of time sufficient to produce the alcohol products or derivatives thereof under such conditions as set forth herein. The reaction conditions comprise (i) a period of time at a temperature and pressure which cause the carbon monoxide and hydrogen to react to produce the desired product, (ii) a temperature between about 50° C. and 400° C. and (iii) a pressure between about 100 psia (7.0 kg/cm$^2$) and 15,000 psia (1,054.6 kg/cm$^2$). This invention employs a ruthenium carbonyl complex and an organosilicon compound having at least one bond Si—X, wherein X is a group such that a transition metal can add across its bond to silicon, and at least one carbon residue R which under the prescribed reaction conditions forms an alcohol having one carbon and one oxygen more than that of R, wherein X and R are as hereinafter described.

The process of this invention is distinctive in the nature of the reaction, the selection of materials which comprise the homogeneous liquid phase mixture, and the reaction parameters. As with any technology, this process has undergone evolutionary changes and its further examination will undoubtedly bring more changes, most likely in the form of additional or substitutional steps and/or materials.

Apart from the conditions of the reaction in terms of time, temperature and pressure, the selection of solvent may constitute an important consideration in the most advantageous practice of this invention. The solvent is selected, when employed, such that the solvent is capable of maintaining the ruthenium carbonyl complex in the homogeneous liquid phase mixture throughout the reaction.

This invention employs a ruthenium carbonyl complex which contains carbon monoxide directly bonded to ruthenium (ruthenium carbonyl). The ruthenium compound which is provided to the reaction is not necessarily in a form which will effectively catalyze the reaction even if it contains a carbon monoxide ligand bonded to it. Ruthenium compounds such as ruthenium salts, oxides and carbonyl clusters may be introduced to the reaction in a condition which allows them to be solubilized, and under the conditions of the reaction they are converted into a carbonyl complex which effectively catalyzes the reaction. Factors achieving the catalyst are the reaction parameters and the choice of solvent. Varied reaction conditions and solvents may result in different amounts of the desired products of the process, and different rates, efficiencies and/or yields.

The ruthenium-containing substances which may be employed in the practice of this invention to form the catalyst encompass those which are described, for example, in Gresham, U.S. Pat. No. 2,535,060 at column 2, starting at line 38 to line 48, and ruthenium carbonyl compounds. Ruthenium oxides, such as dioxide, sesquioxide, or tetraoxide, may be converted to the ruthenium carbonyl complex employed in the process of this invention. Ruthenium carbonyl compounds (which include ruthenium carbonyl hydrides or ruthenium carbonyl clusters) are already provided with a carbonyl ligand, and under the conditions of the reaction can be sufficiently changed to achieve the desired catalytic effect. Ruthenium salts such as those of organic acids can be employed in the practice of this invention to produce the catalyst. In addition to those ruthenium compounds described in the aforementioned Gresham patent, one may employ ruthenium compounds of bidentate ligands, allyl complexes, arene complexes, halides, and alkyl complexes. The choice of ruthenium compounds is varied and not critical to this invention. A number of ruthenium complexes are known to be more stable to the presence of carbon monoxide than other ruthenium compounds and the skilled worker can determine which particular ruthenium compound might take longer to initiate a reaction than other ruthenium compounds. On that basis, one can select for the purposes of convenience the particular ruthenium compound to be utilized in forming the catalyst. However, ruthenium which is associated with an organic molecule or complexed with carbon monoxide is most readily solubilized so as to provide a readily available source of the ruthenium carbonyl complex employed in this process.

The selection of the organosilicon compound, i.e. silane, is such that the compound contains: (1) at least one bond between a silicon atom and a group (X) such that a transition metal can add across its bond to silicon, and (2) a carbon residue (R) attached to the silicon atom, i.e. a silicon-carbon bond. R may be most any carbon containing substituent including, but not limited to, alkyl, araalkyl and the like and one, two or three of such R groups may be present in the organosilicon compound. Typical of suitable organosilicon compounds are alkyl silanes, including mono-, di-, and trialkyl silanes, e.g. trihexylsilane, wherein said alkyl substituents may be substituted. Further, the organosilicon compound may comprise a silicon-based polymer having a carbon residue (R) and a group (X). The organosilicon compound is preferably selected such that at least one —Si—H bond is present, i.e. wherein the group "X" is hydrogen. Representative compounds which are suitable for use in the instant process are set forth in E.

Wiberg and E. Amberger, "Hydrides of Elements of Main Groups I–IV", Elsevier, 1971, pages 462–638; and V. Bazant and V. Chvalovsky, "Chemistry of Organosilicon Compounds," vol. 1 of V. Bazant, V. Chvalovsky, and J. Rathousky, "Organosilicon Compounds," Academic Press, 1965, p. 102–151, said disclosures to said suitable organosilicon compounds being incorporated by reference herein. The following are typical of said organosilicon compounds which may be employed herein:

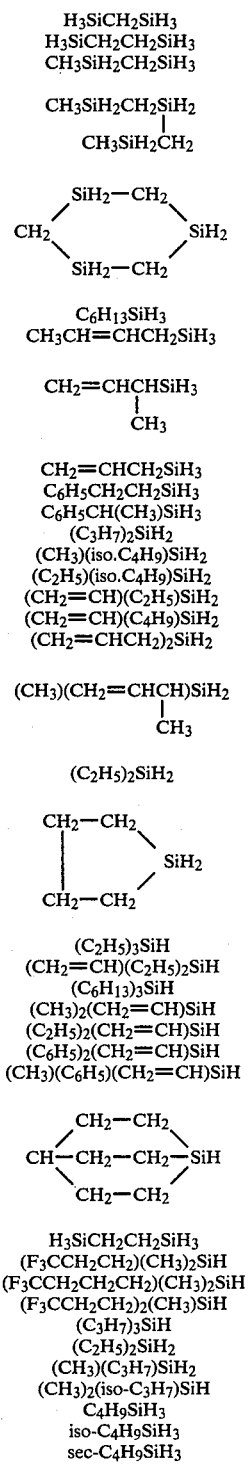

As characterized above, this process is carried out in homogeneous liquid phase mixture. The process is typically carried such that the organosilicon compound is the solvent for the catalyst although a solvent may be employed. The solvent may be solid at room temperature but should, at least in part, be a liquid under the conditions of reaction.

Illustrative of suitable solvents include ketones, esters including lactones, amides including lactams, sulfones, sulfoxides, aromatic hydrocarbons, and the like. Illustrative of specific solvents encompassed by the above classes of solvents are, for example, aromatic hydrocarbons, e.g., benzene, toluene, xylene, naphthalene, alkylnaphthalene, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; anhydrides such as phthalic anhydride, acetic anhydride, etc.; lactams such as N-alkyl caprolactam, such as N-methylcaprolactam, N-alkyl pyrrolidinones such as N-methyl pyrrolidinone, cyclic ureas such as N,N'-dimethylimidazolidone, lactones such as gamma-butyrolactone; amides such as dimethylformamide, dimethylacetamide, hexamethylphophoramide; sulfones such as sulfolane, dimethylsulfone, the substituted sulfolanes described in U.S. Pat. No. 4,224,237; sulfoxides such as dimethylsulfoxide, diphenyl sulfoxide; as well as many others.

Illustrative of other suitable solvents are the ethers, and the like. Illustrative of specific solvents encompassed by the above class of solvent are, for example, ethers such as tetrahydrofuran, tetrahydropyran, diethyl ether, 1,2-dimethoxybenzene, 1,2-diethoxybenezene, the dialkyl ethers of alkylene and polyalkylene glycols, such as ethylene glycol, of 1,2-propylene glycol, of 1,2-butylene glycol, of diethylene glycol, of di-1,2-propylene glycol, of triethylene glycol, of pentaethylene glycol (such as triglyme, tetraglyme and pentaglyme), of di-1,2-butylene glycol, of oxyethylene-oxypropylene glycols, etc., preferably those in which the alkylene group contains 2 and/or 3 carbon atoms in the divalent moiety, such as ethylene and 1,2-propylene, the crown ethers such as described in U.S. Pat. No. 4,162,261, which description of crown ethers, as solvents in that case, are incorporated herein by reference; as well as many others.

In addition, the solvent employed in the practice of this invention may comprise a mixture of two or more of the aforementioned solvents. Which mixtures will achieve what result has not been determined.

The process may be carried out in the presence of a promoter although selection of the promoter is not clearly understood. A promoter, in the context of this invention, is a material provided to the reaction which provides a promotional effect in that it enhances the production (viz., rate, yield, or efficiency) of any of the products, or it improves the selectivity of the reaction toward the alcohol product, or it helps to reduce the loss of ruthenium during the reaction.

The relative amounts of carbon monoxide and hydrogen which are initially present in the reaction mixture can be varied over a wide range. In general, the molar ratio of $CO:H_2$ is in the range of from about 40:1 to about 1:40, suitably from about 20:1 to about 1:20, and preferably from about 10:1 to about 1:10. It is to be understood, however, that molar ratios outside the broadest of these ranges may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention.

The quantity of ruthenium compound and the quantity of organosilicon compound employed are not narrowly critical and can vary over a wide range. In general, the process is desirably conducted in the presence of a catalytically effective quantity of said compounds which gives a suitable and reasonable reaction rate.

The reaction can proceed when employing as little as about $1 \times 10^{-6}$ weight percent, and even lesser amounts, of each material, based on the total weight of reaction mixture (i.e., the liquid phase mixture). The upper concentration limit can be quite high, e.g., about 30 weight percent, and higher of the ruthenium compound and up to about 100 percent by weight of the organosilicon compound e.g., when the organosilicon compound is also employed as the solvent; the realistic upper limit in practicing the invention appears to be dictated and controlled more by economics in view of the cost of ruthenium. Since the rate of conversion of synthesis gas may be dependent upon the concentrations employed, higher concentrations achieving higher rates, large concentrations may prove to be a most desirable embodiment of this invention. Depending on various factors such as the partial pressures of carbon monoxide and hydrogen, the total operative pressure of the system, the operative temperature, the choice of solvent, and other considerations, a catalyst concentration of from about $1 \times 10^{-3}$ to about 20 weight percent of the ruthenium compound and up to about 100 percent by weight of the organosilicon compound, e.g., when the organosilicon catalyst is also employed as the solvent, based on the total weight of reaction mixture, is generally desirable in the practice of the invention. The actual concentration which will provide for the formation of the products will depend on several factors and for a given organosilicon compound under a given set of reactor conditions the concentration may necessarily be greater than $1 \times 10^{-3}$ to provide for the formation of product.

The temperature which may be employed in practicing the process may vary over a wide range of elevated temperatures. In general, the process can be conducted at a temperature between 50° C. and about 400° C. and higher. Temperatures outside this stated range, though not excluded from the scope of the invention, do not fall within certain desirable embodiments of the invention.

The examples below depict batch reactions; however, a continuous gas recycle process can be operated in a similar manner. That is, the batch reactor simulates the continuous reactor except for the gas sparging and continuous gas recycle.

Although this invention has been described with respect to a number of details, it is not intended that this invention should be limited thereby. Moreover, the examples which follow are intended solely to illustrate a variety, including the most favorable, embodiments of this invention and are not intended in any way to limit the scope and intent of this invention.

EXPERIMENTAL PROCEDURE

The following examples, except for examples 9 and 10 and 31 and 32, were carried out according to the following procedure:

A 150 ml. capacity stainless steel reactor capable of withstanding pressures up to 7,000 atmospheres was charged with a premix of a specified organosilicon compound, and a specified amount of a metal compound, as indicated in the examples. The reactor was sealed and charged with a gaseous mixture containing equal molar amounts of carbon monoxide and hydrogen to a specified pressure. Heat was applied to the reactor and its contents; when the temperature of the mixture inside the reactor reached 190° C., as measured by a suitably placed thermocouple, an additional adjustment of carbon monoxide and hydrogen ($H_2:CO=1:1$ mole ratio) was made to bring the pressure back to specified pressure. The temperatures and pressures were maintained as indicated in the examples.

After the reaction was terminated, the vessel and its contents were cooled to room temperature, the excess gas vented and the reaction product mixture was removed. The reactor was then washed with acetone. The reaction mixture and wash were analyzed by use of vapor phase chromatography (VPC) and nuclear magnetic resonance (NMR) after treating the reaction mixture (1.0 g of the reaction mixture) with benzoic anhydride (1.46 grams for examples 1–10 and 33–40; and 0.73 grams for all others) by placing the reaction mixture and the benzoic anhydride in a glass tube which was then sealed with a rubber septum and a cap. The mixture was shaken and then heated to about 250° C. in an oil bath for about 1 hour. The mixture was then cooled to ambient conditions and dissolved in 3 milliliters of $CDCl_3$ prior to analysis by VPC and NMR. The effects of amount of benzoic anhydride, temperature, and reaction time were examined. The aforementioned procedure was believed to adequately combine sufficiency and convenience. The results reported in the Tables are of these analyses, i.e., they are the amounts of benzoate esters expressed as alcohol equivalents. The treatment of the reaction mixture is based on a report [A. Ladenburg, Ber., 5, 319(1872)] of the reaction $Et_3SiOEt + Ac_2O \rightarrow Et_3SiOAc + EtOAc$ ($Et = C_2H_5$; $Ac = acetyl$).

The efficiency of the treatment of the reaction mixture with benzoic anhydride was studied by heating a representative silane (0.40 gram, 3.2 millimoles, of trimethylethoxysilane) with 0.73 gram of benzoic anhydride at 250° C. for 1 hour in a totally-immersed sealed tube. The NMR spectrum of the reaction mixture indicated a 77 percent conversion to ethyl benzoate. Similarly, $(C_6H_{13})_3SiOCH_2CH_2OSi(C_6H_{13})_3$ (0.111 g, 0.177 mmole) was heated with 0.73 g of benzoic anhydride in 1.000 g (3.5 mmoles) of trihexylsilane with a 57 percent conversion to glycol dibenzoate being observed. In addition according to the above procedure, 0.112 grams of $(C_6H_{13})_3SiOCH_2CH_2OSi(C_6H_{13})_3$ and 1.003 grams of trihexylsilane were heated with benzoic anhydride with a 62 percent conversion to glycol dibenzoate being observed.

In examples 9, 10 and 31 and 32 the following procedure was employed:

A 150 ml stainless steel reactor capable of withstanding pressures up to 10,000 psig and containing a removal glass liner was charged with a ruthenium compound (as designated below in the examples). The reactor was purged with carbon monoxide and pressurized with an initial charge of 500 psig (36.19 Kg/cm²) of carbon monoxide. Carbon monoxide and hydrogen (1:1 mole ratio) were then added to the reactor to attain the desired pressure. The reactor was rocked and the contents heated to the reaction temperature and maintained at the reaction temperature for two hours while rocking the reactor. The pressure was maintained at the specified reaction pressure during the indicated period of the reaction by adding carbon monoxide and hydrogen. With these added repressurizations the pressure inside the reactor was maintained at the reaction pressure over the reaction period. The reactor was then cooled and vented. The contents of the reactor were removed and treated as described above.

Example 4 was carried out as indicated under the above-described Experimental Procedure. The reaction mixture was monitored by use of NMR spectroscopy which indicated the progressive disappearance of H bonded to Si and the appearance of products. Results are reported in Table I. VPC analysis of the reaction mixture at 1 hr., 2 hrs., and 4 hrs. indicated the presence of 0, 2.6, and 5.7 grams of n-heptanol, respectively. The reaction mixture at 4 hrs. also contained approximately ~2 grams of methanol, no ethylene glycol (the VPC threshold was a few tenths of a gram; analysis by use of NMR spectroscopy indicated at most a very small amount), no n-hexanol or 2-heptanol, and, perhaps, trace amounts of n-propanol and n-butanol. Distillation of the reaction mixture after 4 hours gave fractions whose VPC's and NMR spectra were consistent with the presence of methanol and n-heptanol. The NMR and mass spectra of the material collected from the VPC and having the VPC retention time of n-heptanol were consistent with the structure of n-heptanol. VPC and NMR analysis of the reaction mixture after treatment of 1.0 g of the 4 hour reaction mixture with benzoic anhydride, as described above, indicated the presence of methyl benzoate and glycol dibenzoate.

A 12.3 g sample of the reaction mixture (at 4 hours) was then reacted with 9.0 g of benzoic anhydride at 250° for 1 hr. Distillation of the resulting mixture gave fractions whose VPC's and NMR spectra were consistent with the presence of methyl benzoate, ethyl benzoate, and ethylene glycol dibenzoate. One of the fractions was washed with aqueous NaOH to remove benzoic acid and benzoic anhydride, which interfered with the VPC analysis for n-heptyl benzoate. The NMR spectrum of the material collected from the VPC of the residue of the distillation, having the retention time of n-heptyl benzoate, was quantitatively consistent with the structure of n-heptyl benzoate.

The preparation of the bis(trihexylsilyl)ether of ethylene glycol was carried out by reacting ethylene glycol (2.4 grams, 0.039 mole) (stirred with NaOH, then distilled at 92° C./10 mm), trihexylchlorosilane (25 grams, 0.078 mole) and pyridine (7.8 milliliters, 0.097 mole) (refluxed over NaOH, then distilled at 113° C. and stored over CaH$_2$) in 47 milliliters of toluene (dried over conventional molecular sieves) according to the procedure described by R. O. Sauer, J. Am. Chem Soc., 66, 1707 (1944) for the preparation of (CH$_3$)$_3$SiOCH$_3$ which is incorporated herein by reference. Five grams of the crude product (having a total weight of about 25 grams) was purified by chromatography using 200 grams of Woelm (TM) silica gel. A final product of at least 1.5 grams was obtained [NMR (CDCl$_3$):3.63 (s,2.0H), 5.6–7.2 (m,39H) ppm upfield from CHCl$_3$; Chemical ionization (isobutane) mass spectrum: calculated for C$_{38}$H$_{82}$O$_2$Si$_2$ 626.5853, for C$_{38}$H$_{82}$O$_2$Si$_2$—C$_6$H$_{13}$ 541.4835; found 626.5198±66 ppm (parent), 541.4828±1.3 ppm (base)].

EXAMPLES 1–5

Examples 1–5 were carried out according to the above described experimental procedure. 80 milliliters of trihexylsilane was reacted at 270° C. for 4 hours under an atmosphere of carbon monoxide and hydrogen (1:1 mole ratio). The pressure employed in each example is set forth in Table I. Examples 1–3 are comparative examples employing only trihexylsilane with no ruthenium compound. The ruthenium compound employed in examples 4 and 5, examples carried out according to this invention, was triruthenium dodecacarbonyl. As shown in Table I, the synergistic combination of the ruthenium compound and the organosilicon compound provides an increase in the amount of methanol and ethylene glycol formed and n-heptanol is formed.

TABLE I

| Example | Ruthenium (Ru) Compound | mmoles of Ru Compound | Pressure (psig) | Product (1 hour)[1] | | | Product (2 hours)[1] | | | Product (4 hours)[1] | | |
|---|---|---|---|---|---|---|---|---|---|---|---|---|
| | | | | Methanol | Glycol[2] | n-heptanol | Methanol | Glycol[2] | n-heptanol | Methanol | Glycol[2] | Heptanol |
| 1 | — | — | 6000 | Trace[3] | — | ND[4] | 0.21 | 0.14 | ND[4] | 0.14 | 0.09 | 0 |
| 2 | — | — | 6300 | Trace | — | ND[4] | Trace | 0 | ND[4] | Very Small | 0 | ≦Very Small |
| 3 | — | — | 8000 | Perhaps Trace | Perhaps Trace | ND[4] | Very Small | Perhaps Trace | ND[4] | 0.23 | 0 | 0 |
| 4 | Ru$_3$(CO)$_{12}$ | 1.0 | 6000 | 1.6 | 0.32 | 10 | 2.2 | 0.54 | 12 | 3.3 | 0.52 | 13 |
| 5 | Ru$_3$(CO)$_{12}$ | 1.0 | 8000 | 1.4 | 0.41 | 5.6 | 2.1 | 0.59 | 12 | 3.9 | 0.64 | 17 |

[1]product is reported in grams and is not corrected for incomplete derivatization.
[2]ethylene glycol
[3]trace indicates that the amount present was just within the lower detection limit of product.
[4]ND = not determined

EXAMPLES 6–8

Examples 6–8 are comparative examples carried out using no organosilicon compound that falls within the scope of this invention with 1.0 millimole of triruthenium dodecacarbonyl at 270° C. for 4 hours using 80 milliliters of solvent (shown in Table II) under 6000 psig of carbon monoxide and hydrogen (1:1 mole ratio).

TABLE II

| Example | Solvent | Product (4 hours)[1] | | Alcohol[6] Product |
|---|---|---|---|---|
| | | Methanol | Glycol | |
| 6 | dibutyl ether | ~0.9 | Trace | ND[4] |
| 7 | tetraethylsilane[3] | ~0.8 | Trace | 0[5] |
| 8 | sulfolane | ~0.6 | Trace | — |

[1]given in grams
[2]ethylene glycol
[3]an organosilicon compound having no silicon-hydrogen bond.
[4]not determined
[5]no n-propanol
[6]alcohol products other than methanol and ethylene glycol.

EXAMPLES 9 and 10

Comparative example 9 and example 10, according to this invention, were carried out by reacting 50 ml of trihexylsilane at 270° C. for 4 hours under a pressure of carbon monoxide and hydrogen (1:1 mole ratio). Example 9 employs no ruthenuim compound. Example 10 employs 0.63 millimole of triruthenuim dodecacarbonyl. Examples 9 and 10 are set forth in Table III.

TABLE III

| Example | Pressure | Product[2] (4 hours) | | |
|---|---|---|---|---|
| | | Methanol | Glycol[1] | n-Heptanol |
| 9 | 4900 | 0.31 | 0 | 0 |
| 10 | 5000 | 3.2 | 0.35 | 11.0 |

[1]ethylene glycol
[2]given in grams

EXAMPLES 11-19

Comparative examples 11-19 were carried out by charging 80 milliliters of trihexylsilane and the metal catalyst shown in Table IV. The reaction was carried out under a carbon monoxide and hydrogen atmosphere (1:1 ratio of $H_2:CO$) under a pressure of 8000 psig for a period of 4 hours. Samples from the reactor were tested at 1 hour, 2 hours and 4 hours after the reaction had begun. The results of comparative examples 11-19 are set forth in Table IV.

EXAMPLES 20-30

Comparative examples 20-30 were carried out by charging the reactor with 80 milliliters of trihexylsilane and dicobalt octacarbonyl. The reaction was carried out under a carbon monoxide and hydrogen atmosphere (1:1 ratio of $H_2:CO$) under the pressures indicated in Table V. Samples from the reactor were tested at 1 hour, 2 hours and 4 hours. The results of comparative examples 20-30 are set forth in Table V.

EXAMPLES 31 AND 32

Comparative examples 31 and 32 were carried out as discussed in the Experimental Procedure for said examples and as set forth in examples 20-30. The results of these examples are set forth in Table VI.

EXAMPLES 33-37

Examples 33-37 were carried out according to this invention by charging the reactor with 80 milliliters of trihexylsilane and 1.0 millimole of $Ru_3(CO)_{12}$ (containing 0.34 gram of carbon monoxide). The reaction was carried out under a carbon monoxide and hydrogen atmosphere for 4 hours at 270°, as indicated in Table VII. The results of these examples are set forth in Table VII.

EXAMPLES 38-40

Examples 38-40 were carried out by charging the reactor with 80 milliliters of sulfolane and 1.0 millimole of $Ru_3(CO)_{12}$. Trihexylsilane was added in an amount as shown in Table VIII. The reaction was carried out under a carbon monoxide and hydrogen atmosphere (1:1 ratio of $H_2:CO$) of 6000 psig at a temperature of 270° C. The results of these examples are set forth in Table VIII.

TABLE IV

| Example | Silane | Metal catalyst[2] | mmoles of catalyst | Product(1hour)[1] | | Product(2hours)[1] | | Product(4hours)[1] | | n-Heptanol[1,6] |
|---|---|---|---|---|---|---|---|---|---|---|
| | | | | MeOH[2] | GLYCOL[2] | MeOH | GLYCOL | MeOH | GLYCOL | |
| 11 | $(C_6H_{13})_3SiH$ | — | — | Perhaps Trace | Perhaps Trace | Very Small | Perhaps Trace | 0.23 (0.5) | — (0.1) | 0 0 |
| 12 | $(C_6H_{13})_3SiH$ | $Rh(CO)_2acac$, | 3.0 | 0.26 | 0.79 | 0.29 | 0.63 | 0.45 | 0.50 | 0 |
| 13[2] | $(C_6H_{13})_3SiH$ | $ClRh(CO)(Ph_3P)_2$, | 3 | Very Small | — | 0.18 | — | 0.33 | — | 0 |
| 14[4] | $(C_6H_{13})_3SiH$ | $Mn_2(CO)_{10}$ | 1.5 | 0.28 | — | 0.18 | — | 0.38 | trace | 0 |
| 15[3] | $(C_6H_{13})_3SiH$ | $Cu_2O$ | 1.5 | Very Small | — | 0.29 | — | 0.28 | trace | 0 |
| 16[4] | $(C_6H_{13})_3SiH$ | $H_2PtCl_6.6H_2O$ | 3 | Small | trace | 0.18 | — | 0.14 | trace | 0 |
| 17 | $(C_6H_{13})_3SiH$ | $H_2OsCl_6.2H_2O$ | 3 | ND[5] | ND[5] | 0.85 | — | 0.31 | — | 0 |
| 18[2] | $(C_6H_{13})_3SiH$ | $[Ph_3P]_2PdCl_2$ | 3 | — | — | Small | — | 0.28 (0.1) | — | 0 |
| 19 | $(C_6H_{13})_3SiH$ | $Co_2(CO)_8$ | 1.5 | 0.38 | 0.62 | 0.49 | 0.76 | 0.56 | 0.50 | 0 |

[1]given in grams and uncorrected for incomplete derivatization. Numbers in parentheses are additional amounts, not subject to correction, found in a small denser phase which accompanied the reaction mixture or in the acetone wash of the reactor.
[2]GLYCOL = ethylene glycol; MeOH = methanol; acac = acetonyl acetonate; Ph = phenyl
[3]copper plates the reactor
[4]gas evolved upon mixing at room temperature
[5]not determined
[6]at 4 hours

TABLE V

| Example | Silane | Metal catalyst | mmoles of catalyst | Product (1 hour)[1] | | Product (2 hours)[1] | | Product (4 hours)[1] | | n-Heptanol[3] | PRESSURE, (psig) |
|---|---|---|---|---|---|---|---|---|---|---|---|
| | | | | MeOH[2] | GLYCOL[2] | MeOH | GLYCOL | MeOH | GLYCOL | | |
| 20 | $(C_6H_{13})_3SiH$ | — | | Trace | 0 | Trace | 0 | Very Small (0.3) | 0 | 0 | 6300 |
| 21 | $(C_6H_{13})_3SiH$ | $Co_2(CO)_8$ | 1.5 | 0.36 | 0.48 | 0.33 | 0.77 | 0.28 (0.2) | 0.73 (0.3) | 0 | 6000 |
| 22 | $(C_6H_{13})_3SiH$ | $Co_2(CO)_8$ | 6 | 0.38 | 0.55 | 0.33 | 0.61 | 0.26 | 0.35 | Trace | 6000 |
| 23[2] | $Ph_3SiH$, 75g | $Co_2(CO)_8$ | 1.5 | 0.19 | Trace | 0.20 | 0.25 | 0.16 (0.1) | 0.12 | 0 $PhCH_2OH^2$ | 6000 |
| 24 | $(C_6H_{13})_3SiH$ | $Co_2(CO)_8$ | 1.5 | 0.38 | 0.62 | 0.49 | 0.76 | 0.52 (0.3) | 0.50 (0.2) | 0 | 8000 |
| 25 | $(C_6H_{13})_3SiH$ | $Co_2(CO)_8$ | 1.5 | 0.36 | 0.48 | 0.33 | 0.77 | 0.28 | 0.73 | 0 | 6000 |
| 26 | $(C_6H_{13})_3SiH$ | $Co_2(CO)_8$ | 1.5 | 0.21 | 0.19 | 0.23 | 0.23 | 0.21 | 0.26 | 0 | 4000 |
| 27 | $(C_6H_{13})_3SiH$ | $Co_2(CO)_8$ | 1.5 | 0 | 0 | Trace | 0 | 0.11 | 0.083 | 0 | ~2400 |

TABLE V-continued

| Example | Silane | Metal catalyst | mmoles of catalyst | Product (1 hour)[1] MeOH[2] | Product (1 hour)[1] GLYCOL[2] | Product (2 hours)[1] MeOH | Product (2 hours)[1] GLYCOL | Product (4 hours)[1] MeOH | Product (4 hours)[1] GLYCOL | n-Heptanol[3] | PRESSURE, (psig) |
|---|---|---|---|---|---|---|---|---|---|---|---|
| 28 | $(C_6H_{13})_3SiH$ | $Co_2(CO)_8$ | 6 | 0.38 | 0.55 | 0.33 | 0.61 | (0.2) 0.26 | (0.3) 0.35 | Trace | 6000 |
| 29 | $(C_6H_{13})_3SiH$ | $Co_2(CO)_8$ | 6 | 0.55 | 0.59 | 0.50 | 0.91 | (0.1) 0.44 | (0.3) 0.76 | Trace | 5000 |
| 30 | $(C_6H_{13})_3SiH$ | $Co_2(CO)_8$ | 6 | 0.69 | 0.51 | 0.45 | 0.46 | (0.4) 0.33 | 0.33 | Trace | 4000 |

[1]given in grams and uncorrected for incomplete derivatization. Numbers in parentheses are additional amounts, not subject to correction, found in a small denser phase which accompanied the reaction mixture or in the acetone wash of the reactor.
[2]GLYCOL = ethylene glycol; MeOH = methanol; Ph = phenyl
[3]at 4 hours

TABLE VI

| Example | Silane | Metal catalyst | mmoles of catalyst | Product (1 hour)[1] MeOH[2] | Product (1 hour)[1] GLYCOL[2] | Product (2 hours)[1] MeOH | Product (2 hours)[1] GLYCOL | Product (4 hours)[1] MeOH | Product (4 hours)[1] GLYCOL | n-Heptanol[3] | PRESSURE, (psig) |
|---|---|---|---|---|---|---|---|---|---|---|---|
| 31 | $(C_6H_{13})_3SiH$ | — | — | ND[4] | ND | ND | ND | 0.31 | 0 | | 4900 |
| 32 | — | $Co_2(CO)_8$ | 1.0 | ND | ND | ND | ND | 0.85 | 0.79 | ND[5] | 5000 |

[1]given in grams and uncorrected for incomplete derivatization. Numbers in parentheses are additional amounts, not subject to correction, found in a small denser phase which accompanied the reaction mixture or in the acetone wash of the reactor.
[2]glycol = ethylene glycol; MeOH = methanol
[3]at 4 hours
[4]ND = not determined

TABLE VII

| Example | $H_2$ Pressure (psig) | CO Pressure (psig) | Product (1 hour)[1] MeOH[4,3] | Product (1 hour)[1] GLYCOL[4] | Product (1 hour)[1] n-Heptanol | Product (2 hours)[1] MeOH[4,3] | Product (2 hours)[1] GLYCOL[4] | Product (2 hours)[1] n-Heptanol | Product (4 hours)[1] MeOH[4,3] | Product (4 hours)[1] GLYCOL[4] | Product (4 hours)[1] n-Heptanol |
|---|---|---|---|---|---|---|---|---|---|---|---|
| 33 | 3000–3500 | — | 0.16 | 0 | Trace | 0.23 | 0 | Trace | 0.17 | 0 | Trace |
| 34 | — | 3500 | 0.10 | 0.04 | ~0.5 | 0.17 | 0.08 | ~1.3 | 0.17 | 0.1 | ~1.3 |
| 35 | 2000 | 2000 | 0.46 | 0.06 | 2.2 | 0.66 | 0.06 | 3.9 | 1.6 | 0.12 | 4.6 |
| 36 | 1000 | 1000 | 0.13 | 0 | 1.7 | 0.12 | 0 | 2.0 | 0.19 | Perhaps Trace | 2.5 |
| 37 | 500 | 500 | Trace | Footnote 2 | 2.1 | Trace | Footnote 2 | 1.3 | 0.08 | Footnote 2 | 1.9 |

[1]Product is reported in grams and is not corrected for incomplete derivatization.
[2]Perhaps a very small amount.
[3]The $Ru_3(Co)_{12}$ contained 0.34g of CO.
[4]MeOH = methanol; GLYCOL = ethylene glycol.

TABLE VIII

| Example | Trihexylsilane, mmoles | Product (1 hour)[1] MeOH[2] | Product (1 hour)[1] GLYCOL[2] | Product (1 hour)[1] n-Heptanol | Product (2 hours)[1] MeOH[2] | Product (2 hours)[1] GLYCOL[2] | Product (2 hours)[1] n-Heptanol | Product (4 hours)[1] MeOH[2] | Product (4 hours)[1] GLYCOL[2] | Product (4 hours)[1] n-Heptanol |
|---|---|---|---|---|---|---|---|---|---|---|
| 38 | — | ~0.15 | 0 | 0 | ~0.3 | 0 | 0 | ~0.6 | trace | Footnote 3 |
| 39 | 3 | ~0.12 | 0 | 0 | ~0.3 | 0 | 0 | ~0.7 | 0 | 0 |
| 40 | 30 | ~0.14 | 0 | 0 | ~0.3 | 0 | 0 | ~0.7 | 0 | 0 |

[1]Product is reported in grams and is not corrected for incomplete derivatization.
[2]MeOH = methanol; GLYCOL = ethylene glycol
[3]perhaps a very small amount

What is claimed is:

1. The process for making alcohols having one carbon and one oxygen more than the carbon residue of an organosilicon compound comprising reacting in the homogeneous liquid phase an organosilicon compound having bonded to silicon a carbon residue (R) and a group (X) wherein said group (X) is such that a transition metal can add across its bond to silicon, with carbon monoxide and hydrogen in the presence of an effective amount of a ruthenium carbonyl complex at a temperature and pressure sufficient to form alcohol products having one carbon and one oxygen more than the carbon residue (R) of said organosilicon compound.

2. The process of claim 1 wherein X is hydrogen.

3. The process of claim 1 wherein the organosilicon compound is a mono-, di-, or tri-alkyl silane.

4. The process of claim 1 wherein the pressure is between about 100 psia (7.0 Kg/cm$^2$) and 15,000 psia (1,054.6 Kg/cm$^2$).

5. The process of claim 1 wherein the temperature is between about 50° C. and about 400° C.

6. The process of claim 1 wherein a solvent is employed.

7. The process of claim 1 wherein unreacted carbon monoxide and hydrogen are recycled to the liquid phase.

* * * * *

UNITED STATES PATENT AND TRADEMARK OFFICE
CERTIFICATE OF CORRECTION

PATENT NO. : 4,345,103
DATED : August 17, 1982
INVENTOR(S) : Leonard Kaplan

It is certified that error appears in the above—identified patent and that said Letters Patent is hereby corrected as shown below:

Col. 16, Table VIII, for Example 39, the third from the last entry appearing "∼0.7" should read --∼0.6--.

Signed and Sealed this

Fifteenth Day of February 1983

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,345,103
DATED : August 17, 1982
INVENTOR(S) : Leonard Kaplan

It is certified that error appears in the above—identified patent and that said Letters Patent is hereby corrected as shown below:

Column 14, line 5, "and 32" should be deleted.

Column 14, line 6, "and 32 were" should be deleted.

Column 14, line 9, "these examples" should appear --this example--.

Column 15, Table VI, the line identified by Example 32 should be deleted.

Signed and Sealed this

Seventeenth Day of April 1984

[SEAL]

Attest:

GERALD J. MOSSINGHOFF

Attesting Officer

Commissioner of Patents and Trademarks